United States Patent
Yang et al.

(10) Patent No.: US 11,993,567 B2
(45) Date of Patent: May 28, 2024

(54) METHOD FOR PREPARING ALDEHYDE AND APPARATUS FOR PREPARING ALDEHYDE

(71) Applicant: LG CHEM, LTD., Seoul (KR)

(72) Inventors: Jusang Yang, Daejeon (KR); Sangjun Shin, Daejeon (KR); Sungshik Eom, Daejeon (KR); Tae Yun Kim, Daejeon (KR); Dong Hyun Ko, Daejeon (KR); Sungpil Yang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 304 days.

(21) Appl. No.: 17/641,716

(22) PCT Filed: Aug. 26, 2021

(86) PCT No.: PCT/KR2021/011424
§ 371 (c)(1),
(2) Date: Mar. 9, 2022

(87) PCT Pub. No.: WO2022/059959
PCT Pub. Date: Mar. 24, 2022

(65) Prior Publication Data
US 2022/0402846 A1    Dec. 22, 2022

(30) Foreign Application Priority Data

Sep. 17, 2020 (KR) .................. 10-2020-0119657

(51) Int. Cl.
*C07C 45/50* (2006.01)
*B01J 8/10* (2006.01)
*B01J 31/12* (2006.01)
*B01J 31/18* (2006.01)
*C07C 45/82* (2006.01)

(52) U.S. Cl.
CPC ............... *C07C 45/505* (2013.01); *B01J 8/10* (2013.01); *B01J 31/122* (2013.01); *B01J 31/185* (2013.01); *C07C 45/82* (2013.01)

(58) Field of Classification Search
CPC ............ C07C 45/50; B01J 8/10; B01J 31/185
See application file for complete search history.

(56) References Cited

U.S. PATENT DOCUMENTS

| | | | |
|---|---|---|---|
| 4,247,486 A | 1/1981 | Brewester et al. | |
| 5,053,551 A | 10/1991 | Harrison et al. | |
| 8,404,903 B2 * | 3/2013 | Cox | C07C 45/50 568/454 |
| 2003/0013919 A1 | 1/2003 | Walczuch et al. | |
| 2004/0138508 A1 | 7/2004 | Tinge et al. | |
| 2011/0269997 A1 | 11/2011 | Cox et al. | |
| 2012/0103786 A1 | 5/2012 | Gayet et al. | |
| 2019/0023637 A1 | 1/2019 | Simpson et al. | |

FOREIGN PATENT DOCUMENTS

| | | |
|---|---|---|
| CN | 104001548 | 8/2014 |
| CN | 106278844 | 1/2017 |
| JP | 2011-528331 A | 11/2011 |
| JP | 2019-508450 A | 3/2019 |
| KR | 10-1995-0012999 B1 | 10/1995 |
| KR | 10-2003-0094344 A | 12/2003 |
| KR | 10-2010-0058712 A | 6/2010 |
| KR | 10-2011-0047189 A | 5/2011 |
| KR | 10-2011-0135159 A | 12/2011 |
| WO | 2001-058844 A2 | 8/2001 |
| WO | 2017083106 A1 | 5/2017 |

* cited by examiner

*Primary Examiner* — Sikarl A Witherspoon
(74) *Attorney, Agent, or Firm* — Bryan Cave Leighton Paisner LLP

(57) ABSTRACT

A method for preparing an aldehyde including forming a reaction product including an aldehyde by reacting an olefin-based compound with a synthetic gas in a hydroformylation reactor in the presence of a hydroformylation catalyst; introducing the reaction product including the aldehyde to a vaporizer; separating low-boiling point components of the reaction product from an upper part of a vaporizer catch pot included in the vaporizer; separating high-boiling point components of the reaction product from a lower part of the vaporizer catch pot; and recirculating at least a portion of the low-boiling point components separated from an upper part of the vaporizer catch pot back to the vaporizer.

12 Claims, 3 Drawing Sheets

[FIG. 1]
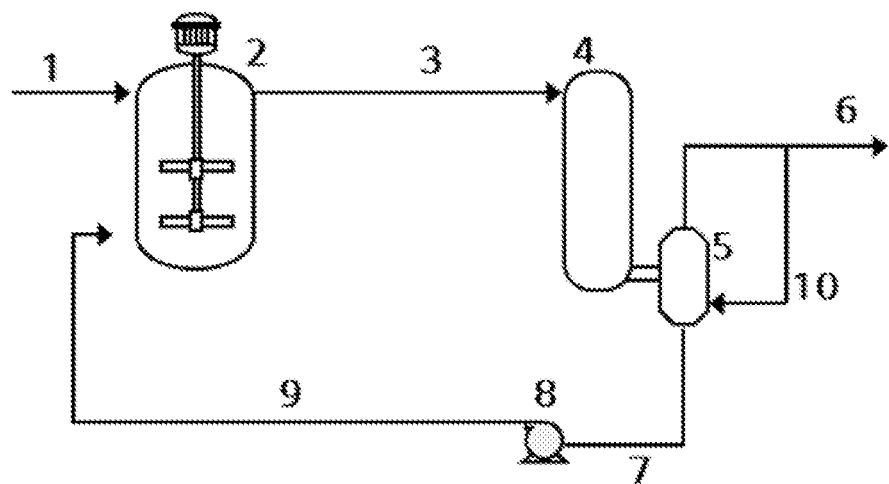
[FIG. 2]
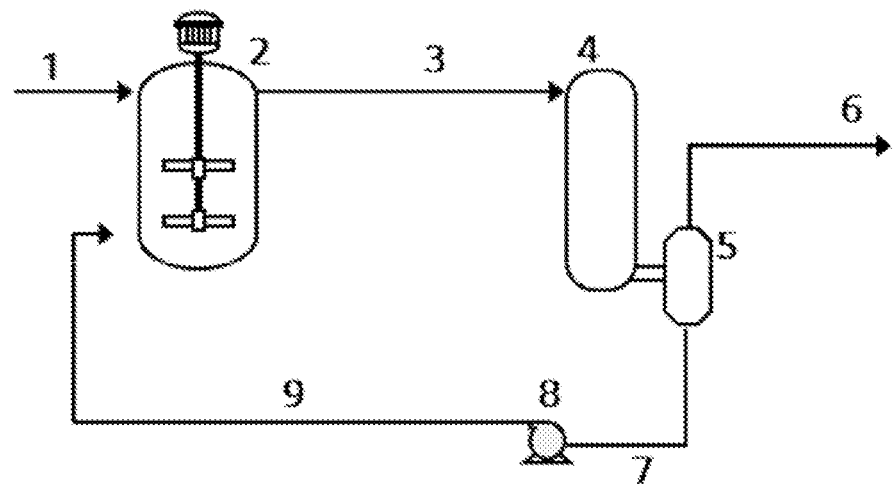

[FIG. 3]
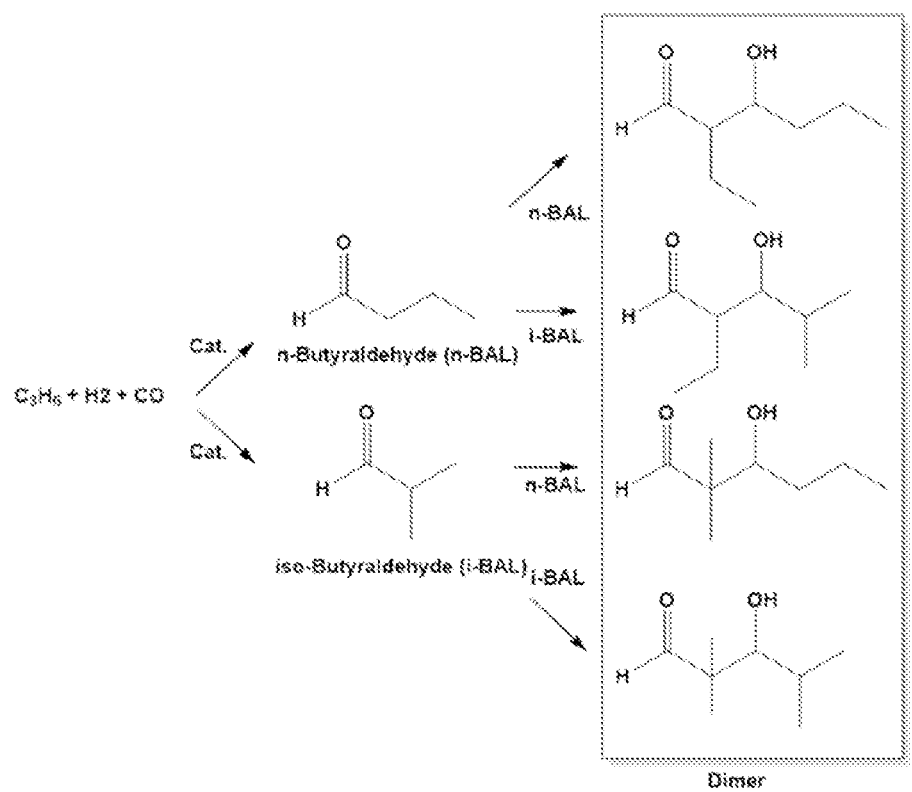

[FIG. 4]
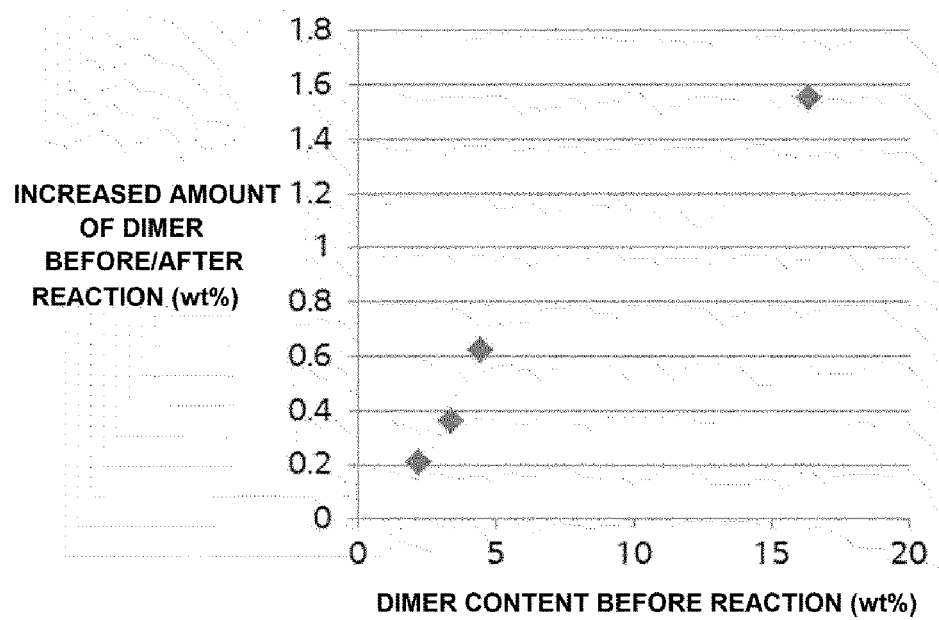

METHOD FOR PREPARING ALDEHYDE AND APPARATUS FOR PREPARING ALDEHYDE

CROSS-REFERENCE TO RELATED APPLICATIONS

This application is a U.S. national stage of international Application No. PCT/KR2021/011424, filed on Aug. 26, 2021, and claims priority to and the benefits of Korean Patent Application No. 10-2020-0119657, filed with the Korean Intellectual Property Office on Sep. 17, 2020, the entire contents of which are incorporated by reference as if fully set forth herein.

FIELD

The present application relates to a method for preparing an aldehyde, and an apparatus for preparing an aldehyde.

BACKGROUND

A hydroformylation reaction, which includes reacting various olefins with carbon monoxide (CO) and hydrogen ($H_2$), commonly referred to as a synthetic gas, in the presence of a homogeneous organometal catalyst and a ligand to produce a linear (normal) and branched (iso) aldehyde having the number of carbon atoms increased by one was first discovered by Otto Roelen of Germany in 1938.

The hydroformylation reaction, generally known as an oxo reaction, is \industrially very important in a homogeneous catalyst reaction, and various aldehydes comprising alcohol derivatives are produced through the oxo process and consumed worldwide.

Various aldehydes synthesized through the oxo reaction are sometimes oxidized or hydrogenated after a condensation reaction such as an aldol condensation, and modified to various acids and alcohols comprising a long alkyl group. Particularly, a hydrogenated alcohol of an aldehyde produced by such an oxo reaction is referred to as an oxoalcohol, and the oxo-alcohol is widely used industrially as solvents, additives, raw materials of various plasticizers, synthetic lubricants and the like.

Catalysts currently used in the oxo process are mainly of the cobalt (Co) and rhodium (Rh) series, and normal/iso selectivity (ratio of linear (normal) to branched (iso) isomers) of an aldehyde produced using these catalysts varies depending on the types of ligand used and the operating conditions. Currently, 70% or more of oxo plants around the world are adopting a low pressure oxo process using a rhodium-based catalyst.

As a central metal of the oxo catalyst, iridium (Ir), ruthenium (Ru), osmium (Os), platinum (Pt), palladium (Pd), iron (Fe), nickel (Ni) and the like may be used in addition to cobalt (Co) and rhodium (Rh). However, these metals are known to exhibit catalytic activity in the order of Rh>>Co>Ir, Ru>Os>Pt>Pd>Fe>Ni and the like, and accordingly, most processes and studies are focused on rhodium and cobalt.

As the ligand, phosphine ($PR_3$, where R is $C_6H_5$ or $n\text{-}C_4H_9$), phosphine oxide ($O=P(C_6H_5)_3$), phosphite, amine, amide, isonitrile, and the like, may be used.

A representative example of hydroformylation may additional comprise preparing octanol (2-ethylhexanol) from propylene using a rhodium-based catalyst.

Octanol is mainly used as a raw material in the preparation of a PVC plasticizer such as DOP (dioctyl phthalate), and in addition thereto, is used as an intermediate material for synthetic lubricants, surfactants and the like. Propylene is introduced into an oxo reactor using a catalyst together with a synthetic gas ($CO/H_2$) to produce normal-butyraldehyde and iso-butyraldehyde. The produced aldehyde mixture is sent to a separation system with a catalyst mixture and separated into a hydrocarbon and a catalyst mixture, and then the catalyst mixture is circulated to the reactor, and the hydrocarbon component is transferred to a stripper. The hydrocarbon of the stripper is stripped by a newly supplied synthetic gas to recover unreacted propylene and synthetic gas, which is sent to the oxo reactor, and the butyraldehyde is transferred to a fractionating column and separated into normal- and iso-butyraldehyde. The normal-butyraldehyde at the bottom of the fractionating column is introduced to an aldol condensation reactor to produce 2-ethylhexanal using a condensation and dehydration reaction, then transferred to a hydrogenation reactor, and octanol (2-ethylhexanol) is produced by hydrogenation. The reactants at the outlet of the hydrogenation reactor are transferred to a fractionating column, and an octanol product is produced after separating soft/hard ends.

The hydroformylation reaction may be conducted continuously, semi-continuously or batch-wise, and a typical hydroformylation reaction process is a gas or liquid recirculation system. In the hydroformylation reaction, it is important to increase reaction efficiency by allowing starting materials formed in liquid and gaseous phases to smoothly contact each other. For this purpose, a continuous stirred tank reactor (CSTR), which stirs components in liquid and gaseous phases in the reactor to bring them evenly in contact with each other, has been mainly used in the art.

In this regard, most studies on the catalysts in the art have been conducted to increase a ratio of a linear aldehyde derivative (normal-aldehyde) since the linear aldehyde derivative has a higher value among aldehydes produced by an oxo reaction. However, as demands for isoaldehydes have recently increased with the development of compounds using a branched aldehyde derivative (iso-aldehyde), for example, isobutyric acid, neopentyl glycol (NPG), 2,2,4-trimethyl-1,3-pentanediol, isovaleric acid, and the like, studies to increase selectivity of the branched aldehyde derivative have been continuously conducted.

SUMMARY

The present application is directed to a method for preparing an aldehyde, and an apparatus for preparing an aldehyde.

An exemplary embodiment of the present application is a method for preparing an aldehyde, the method comprising:

forming a reaction product comprising an aldehyde by reacting an olefin-based compound with a synthetic gas in a hydroformylation reactor in the presence of a catalyst for a hydroformylation reaction;

introducing the reaction product comprising an aldehyde into a vaporizer;

separating low-boiling point components of the reaction product to an upper part of a vaporizer catch pot present in the vaporizer, and separating high-boiling point components of the reaction product to a lower part of the vaporizer catch pot; and recirculating at least a portion of the low-boiling point components separated from an upper part of the vaporizer catch pot back to the vaporizer catch pot, wherein a weight of the low-boiling point components recirculated to the vaporizer catch pot is from 0.1 times to 10 times a weight of the high-boiling point components separated from a lower part of the vaporizer catch pot.

In addition, another exemplary embodiment of the present application provides a method for separating an aldehyde, the method comprising:

introducing a composition comprising low-boiling point components comprising an aldehyde and high-boiling point components comprising a catalyst solution for a hydroformylation reaction to a vaporizer comprising a vaporizer catch pot;

separating the low-boiling point components comprising an aldehyde to an upper part of the vaporizer catch pot, and separating the high-boiling point components comprising a catalyst solution for a hydroformylation reaction to a lower part of the vaporizer catch pot; and recirculating at least a portion of the low-boiling point components separated from an upper part of the vaporizer catch pot back to the vaporizer catch pot, wherein a weight of the low-boiling point components recirculated to the vaporizer catch pot is from 0.1 times to 10 times a weight of the high-boiling point components separated from a lower part of the vaporizer catch pot.

In addition, another exemplary embodiment of the present application is an apparatus for preparing an aldehyde, the apparatus comprising:

a hydroformylation reactor comprising a reactant supply pipe and a reaction product moving pipe;

a vaporizer connected to the reaction product moving pipe of the hydroformylation reactor and comprising a vaporizer catch pot;

a low-boiling point component pipe provided at an upper part of the vaporizer catch pot, and a high-boiling point component pipe provided at a lower part of the vaporizer catch pot; and a low-boiling point recirculation pipe connecting the low-boiling point component pipe and the vaporizer catch pot.

A method for preparing an aldehyde according to an exemplary embodiment of the present application comprises recirculating at least a portion of low-boiling point components separated from an upper part of a vaporizer catch pot back to the vaporizer catch pot. Accordingly, a concentration of high-boiling point components present in a section from the vaporizer catch pot to a hydroformylation reactor through a high-boiling point recirculation pipe can be lowered, a temperature of the solution can be lowered, and a time taken to reach the hydroformylation reactor can be reduced, and as a result, a content of an aldehyde dimer that can be synthesized in the section reaching the hydroformylation reactor through the high-boiling point recirculation pipe can be reduced.

According to an exemplary embodiment of the present application, the amount of produced aldehyde dimer can be reduced, and therefore, a reaction yield of the aldehyde preparation process can be enhanced.

BRIEF DESCRIPTION OF DRAWINGS

FIG. 1 is an illustration of an apparatus for preparing an aldehyde according to an exemplary embodiment of the present application.

FIG. 2 is an illustration of an existing apparatus for preparing an aldehyde.

FIG. 3 is a schematic representation of dimer formation of butyraldehyde, a product of a hydroformylation reaction.

FIG. 4 is a graphical representation of the amount of aldehyde dimers of examples and comparative examples of the present application.

REFERENCE NUMERALS

1: Reactant Supply Pipe
2: Hydroformylation Reactor
3: Reaction Product Moving Pipe
4: Vaporizer
5: Vaporizer Catch Pot
6: Low-Boiling Point Component Pipe
7: High-Boiling Point Component Pipe
8: Circulation Pump
9: High-Boiling Point Component Recirculation Pipe
10: Low-Boiling Point Component Recirculation Pipe

DETAILED DESCRIPTION

Hereinafter, the present application will be described in more detail.

In the present specification, a description of a certain member being placed "on" another member comprises not only a case of the certain member being in contact with the another member but a case of still another member being present between the two members.

In the present specification, a description of a certain part "comprising" certain constituents means capable of further comprising other constituents, and does not exclude other constituents unless particularly stated on the contrary.

As illustrated in FIG. 3, butyraldehyde is produced when hydroformylation is carried out with propylene, hydrogen and carbon monoxide in the presence of a catalyst. The resulting butyraldehyde has a normal form and an iso form, and each of the two butyraldehydes may further go through an aldol reaction with each other to produce an aldehyde dimer. Particularly, aldehyde not discharged through a low-boiling point component pipe of a vaporizer after the hydroformylation reaction may produce an aldehyde dimer through an aldol reaction, and the resulting aldehyde dimer reduces a reaction yield of a target aldehyde in an aldehyde preparation process.

In addition, in a pipe recirculated from a vaporizer to a hydroformylation reactor, high-boiling point components are concentrated, and accordingly, high-boiling point components are recirculated to the reactor comprising a certain amount of aldehyde under a condition of certain temperature or higher to prevent catalyst precipitation. During this process, an aldehyde dimer content increases because of a larger amount of aldehyde going through an aldol reaction.

In order to resolve the above-described problems, the present application attempts to reduce the amount of aldehyde dimer production that may reduce a reaction yield of an aldehyde preparation process.

A method for preparing an aldehyde according to an exemplary embodiment of the present application comprises forming a reaction product comprising an aldehyde by reacting an olefin-based compound with a synthetic gas in a hydroformylation reactor in the presence of a catalyst for a hydroformylation reaction; introducing the reaction product comprising an aldehyde to a vaporizer; separating low-boiling point components of the reaction product to an upper part of a vaporizer catch pot comprised in the vaporizer, and separating high-boiling point components of the reaction product to a lower part of the vaporizer catch pot; and recirculating at least a portion of the low-boiling point components separated from an upper part of the vaporizer catch pot back to the vaporizer catch pot, wherein a weight of the low-boiling point components recirculated to the vaporizer catch pot is from 0.1 times to 10 times a weight of the high-boiling point components separated from a lower part of the vaporizer catch pot.

In addition, a method for separating an aldehyde according to an exemplary embodiment of the present application comprises introducing a composition comprising low-boiling point components comprising an aldehyde and high-boiling point components comprising a catalyst solution for a hydroformylation reaction to a vaporizer comprising a vaporizer catch pot; separating the low-boiling point components comprising an aldehyde to an upper part of the vaporizer catch pot, and separating the high-boiling point components comprising a catalyst solution for a hydroformylation reaction to a lower part of the vaporizer catch pot; and recirculating at least a portion of the low-boiling point components separated from an upper part of the vaporizer catch pot to the vaporizer catch pot, wherein a weight of the low-boiling point components recirculated to the vaporizer catch pot is from 0.1 times to 10 times a weight of the high-boiling point components separated from a lower part of the vaporizer catch pot.

In an exemplary embodiment of the present application, the low-boiling point components separated from an upper part of the vaporizer catch pot may comprise an aldehyde, an unreacted olefin-based compound and a synthetic gas. Herein, at least a portion of the low-boiling point components separated from an upper part of the vaporizer catch pot is recirculated back to the vaporizer catch pot. By recirculating at least a portion of the low-boiling point components separated from an upper part of the vaporizer catch pot back to the vaporizer catch pot, the recirculated low-boiling point components are mixed with the high-boiling point components present in the vaporizer catch pot, which may reduce a concentration of the high-boiling point components. Accordingly, the concentration of the high-boiling point components present in a section from the vaporizer catch pot to the hydroformylation reactor through the high-boiling point recirculation pipe may be reduced, a temperature of the solution may be lowered, and a time taken to reach the hydroformylation reactor may be reduced. As a result, a content of an aldehyde dimer that may be synthesized in the section reaching the hydroformylation reactor through the high-boiling point recirculation pipe may be reduced.

In an exemplary embodiment of the present application, the weight of the low-boiling point components recirculated to the vaporizer catch pot may be 0.1 times to 10 times, and may be 1 time to 8 times the weight of the high-boiling point components separated from a lower part of the vaporizer catch pot. When satisfying the weight range of the low-boiling point components recirculated to the vaporizer catch pot, a content of an aldehyde dimer that may be synthesized in the section reaching the hydroformylation reactor through the high-boiling point recirculation pipe may be reduced.

In addition, when the weight of the low-boiling point components recirculated to the vaporizer catch pot is less than 0.1 times the weight of the high-boiling point components separated from a lower part of the vaporizer catch pot, an effect of reducing the amount of produced aldehyde dimer described above is insignificant, and the reaction yield may decrease by consuming an aldehyde that is a product of the hydroformylation reaction. In addition, when the weight of the low-boiling point components recirculated to the vaporizer catch pot is greater than 10 times the weight of the high-boiling point components separated from a lower part of the vaporizer catch pot, a concentration of the catalyst component introduced to the hydroformylation reactor through the high-boiling point recirculation pipe becomes too low reducing hydroformylation reactivity.

In an exemplary embodiment of the present application, the high-boiling point components separated from a lower part of the vaporizer catch pot may comprise an aldehyde dimer and a catalyst for a hydroformylation reaction. Herein, the high-boiling point components separated from a lower part of the vaporizer catch pot may be recirculated to the hydroformylation reactor. As illustrated in FIG. 3, the aldehyde dimer is produced by two aldehydes going through an aldol condensation reaction with each other.

In an exemplary embodiment of the present application, by recirculating at least a portion of the low-boiling point components separated from an upper part of the vaporizer catch pot back to the vaporizer catch pot, the recirculated low-boiling point components are mixed with the high-boiling point components present in the vaporizer catch pot, which may reduce a concentration of the high-boiling point components.

In an exemplary embodiment of the present application, the aldehyde dimer content may be 10% by weight or less, may be 5% by weight or less, and may be 1% by weight or greater based on a total weight of the high-boiling point components separated from a lower part of the vaporizer catch pot. The aldehyde dimer content being greater than 10% by weight based on a total weight of the high-boiling point components separated from a lower part of the vaporizer catch pot is not preferred since the amount of produced aldehyde increases in the high-boiling point recirculation pipe, which may increase the aldehyde dimer content in the hydroformylation reactor.

In an exemplary embodiment of the present application, the vaporizer catch pot may have a temperature of 50° C. to 100° C., and 55° C. to 90° C. In addition, the vaporizer catch pot may have a pressure of atmospheric pressure to 5 bar, and atmospheric pressure to 3 bar. Herein, the atmospheric pressure means normal pressure, and means a pressure when not particularly increased or decreased. When satisfying the temperature range and the pressure range of the vaporizer catch pot, the aldehyde dimer content may be reduced.

In an exemplary embodiment of the present application, the catalyst for a hydroformylation reaction may comprise a phosphite ligand represented by Chemical Formula 1 and a transition metal compound represented by Chemical Formula 2:

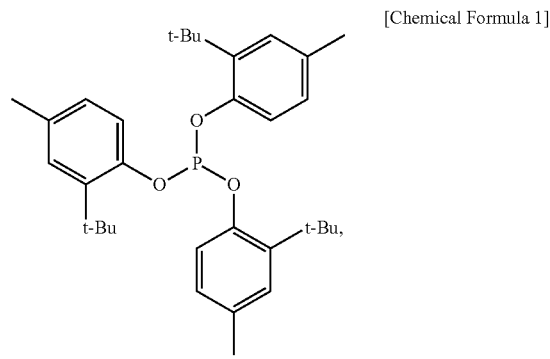

[Chemical Formula 1]

[Chemical Formula 2]

$M(L1)x(L2)y(L3)z$.

In Chemical Formula 2:

M is cobalt (Co), rhodium (Rh), iridium (Ir), ruthenium (Ru), iron (Fe), nickel (Ni), palladium (Pd), platinum (Pt) or osmium (Os), L1, L2 and L3 are the same as or different from each other, and each is independently hydrogen, carbonyl (CO), cyclooctadiene, norbornene, chlorine, triphenylphosphine (TPP) or acetylacetonato (AcAc), and x, y and z are each independently from 0 to 5, and x, y and z are not 0 at the same time.

In an exemplary embodiment of the present application, a content of the transition metal compound represented by Chemical Formula 2 may be from 0.003 moles to 0.05 moles, may be from 0.004 moles to 0.045 moles, and may be from 0.0042 moles to 0.042 moles, based on 1 mole of the phosphite ligand represented by Chemical Formula 1. When the content of the transition metal compound represented by Chemical Formula 2 satisfies 0.003 moles to 0.05 moles based on 1 mole of the phosphite ligand represented by Chemical Formula 1, activity of the catalyst for the hydroformylation reaction may be superior, and the catalyst activity and stability may be reduced when the content is outside the above-mentioned ranges.

The transition metal compound represented by Chemical Formula 2 may be one or more types selected from the group consisting of cobalt carbonyl ($Co_2(CO)_8$), rhodium acetylacetonato dicarbonyl ($Rh(AcAc)(CO)_2$), rhodium acetylacetonato carbonyl triphenylphosphine ($Rh(AcAc)(CO)(TPP)$), hydridocarbonyl tri(triphenylphosphine)rhodium [$HRh(CO)(TPP)_3$], iridium acetylacetonato dicarbonyl ($Ir(AcAc)(CO)_2$) and hydridocarbonyl tri(triphenylphosphine) iridium ($HIr(CO)(TPP)_3$).

In an exemplary embodiment of the present application, the olefin-based compound may be represented by the following Chemical Formula 3:

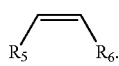

[Chemical Formula 3]

In Chemical Formula 3:

$R_5$ and $R_6$ are the same as or different from each other, and each is independently hydrogen, an alkyl group, fluorine (F), chlorine (Cl), bromine (Br), trifluoromethyl (—$CF_3$), or a substituted or unsubstituted aryl group.

The aryl group may be unsubstituted or substituted with one or more types of substituents of nitro (—$NO_2$), fluorine (F), chlorine (Cl), bromine (Br), methyl, ethyl, propyl and butyl.

More specifically, the olefin-based compound may be one or more types selected from the group consisting of ethylene, propylene, 1-butene, 1-pentene, 1-hexene, 1-octene and styrene.

In an exemplary embodiment of the present application, the olefin-based compound may be propylene, and the aldehyde may be butyraldehyde.

In an exemplary embodiment of the present application, the hydroformylation reaction may be carried out using a method of dissolving the transition metal compound represented by Chemical Formula 2 and the phosphite ligand represented by Chemical Formula 1 in a solvent to prepare a mixed solution of the transition metal compound and the phosphite ligand, that is, a catalyst composition, injecting the olefin-based compound represented by Chemical Formula 3 and a synthetic gas together with the catalyst composition, and stirring the result while raising a temperature and applying a pressure.

The solvent may be one or more types selected from the group consisting of propane aldehyde, butyraldehyde, pentyl aldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride and heptane.

In an exemplary embodiment of the present application, the step of reacting the olefin-based compound with a synthetic gas in the hydroformylation reactor may be conducted at a temperature of 50° C. to 90° C. and a pressure of 5 bar to 25 bar, and may be conducted at a temperature of 55° C. to 85° C. and a pressure of 8 bar to 18 bar. When the temperature in the hydroformylation reaction step is lower than 50° C., reactivity may significantly decrease, and when the temperature is higher than 90° C., the content of heavies increases thereby decreasing the yield. In addition, when the pressure in the hydroformylation reaction step is less than 5 bar, reactivity may significantly decrease, and when the pressure is greater than 25 bar, the cost and design of the apparatus may increase.

In an exemplary embodiment of the present application, the olefin-based compound:the synthetic gas may have a molar ratio of 95:5 to 5:95, and 75:25 to 25:75 in the hydroformylation reaction step. When the olefin-based compound:the synthetic gas has a molar ratio of 95:5 to 5:95 in the hydroformylation reaction step, activity of the catalyst for the hydroformylation reaction may be superior, and the molar ratio being outside the above-mentioned range may reduce catalyst activity and stability.

In addition, an apparatus for preparing an aldehyde according to an exemplary embodiment of the present application comprises a hydroformylation reactor comprising a reactant supply pipe and a reaction product moving pipe; a vaporizer connected to the reaction product moving pipe of the hydroformylation reactor and comprising a vaporizer catch pot; a low-boiling point component pipe provided at an upper part of the vaporizer catch pot, and a high-boiling point component pipe provided at a lower part of the vaporizer catch pot; and a low-boiling point recirculation pipe connecting the low-boiling point component pipe and the vaporizer catch pot.

In an exemplary embodiment of the present application, the apparatus may further comprise a high-boiling point recirculation pipe connecting the high-boiling point component pipe and the hydroformylation reactor.

FIG. 1 is a schematic illustration of an apparatus for preparing an aldehyde according to an exemplary embodiment of the present application, and FIG. 2 is a schematic illustration of an existing apparatus for preparing an aldehyde.

As illustrated in FIG. 1, the apparatus for preparing an aldehyde according to an exemplary embodiment of the present application comprises a hydroformylation reactor (2) comprising a reactant supply pipe (1) and a reaction product moving pipe (3); a vaporizer (4) connected to the reaction product moving pipe (3) of the hydroformylation reactor (2) and comprising a vaporizer catch pot (5); a low-boiling point component pipe (6) provided at an upper part of the vaporizer catch pot (5), and a high-boiling point component pipe (7) provided at a lower part of the vaporizer catch pot (5); and a low-boiling point recirculation pipe (10) connecting the low-boiling point component pipe (6) and the vaporizer catch pot (5). Herein, the apparatus for preparing an aldehyde may further comprise a high-boiling point recirculation pipe (9) connecting the high-boiling point component pipe (7) and the hydroformylation reactor (2). The vaporizer (4) and the vaporizer catch pot (5) may be directly connected to each other. For example, an outlet of the vaporizer (4) may become an inlet of the vaporizer catch pot (5).

Hereinafter, the present application will be described in detail with reference to examples in order to specifically describe the present application. However, examples according to the present application may be modified in various different forms, and the scope of the present application is not construed as being limited to the examples described below. Examples of the present application are provided in order to more fully describe the present application to those having average knowledge in the art.

EXAMPLES

Example 1

Rhodium acetylacetonato carbonyl triphenylphosphine (Rh(AcAc)(CO)(TPP), ROPAC) and tris(2-tert-butyl-4-methylphenyl)phosphite (TTBMPP) were used as a catalyst.

A high-boiling point component solution comprising ROPAC and TTBMPP was dissolved in a butyraldehyde solution, a low-boiling point component, to prepare an aldehyde solution (100 g) having a concentration as shown in Table 1, and the aldehyde solution was introduced to a 600 mL autoclave reactor. After introducing the aldehyde solution, the autoclave reactor was pressurized to 1.8 bar using nitrogen, and the reaction was carried out for 2 hours at 65° C. at a stirring rate of 1,000 rpm. The reaction solution was sampled every 30 minutes, and content of each of the organic matters was analyzed by gas chromatography (GC).

Example 1 sets a condition of a vaporizer catch pot and a high-boiling point recirculation pipe. In other words, Example 1 sets a process condition in which at least a portion of the low-boiling point components separated from an upper part of a vaporizer catch pot is recirculated back to the vaporizer catch pot. Herein, a weight of the low-boiling point components recirculated to the vaporizer catch pot was set to 6.43 times a weight of the high-boiling point components separated from a lower part of the vaporizer catch pot.

Examples 2 and 3 and Comparative Example 1

Reaction solutions were prepared in the same manner as in Example 1 except that the weight of the low-boiling point components recirculated to the vaporizer catch pot was adjusted as shown in Table 1:

TABLE 1

| | Component Content (Based on Weight of High-Boiling Point Components Separated to Lower Part of Vaporizer Catch Pot) | | | |
|---|---|---|---|---|
| | ROPAC Content (ppm) | TTBMPP Content (% by Weight) | Aldehyde Dimer Content (% by Weight) | Weight of Recirculated Low-Boiling Point Components |
| Example 1 | 75 | 6 | 2.20 | 6.43 Times |
| Example 2 | 75 | 6 | 3.38 | 3.84 Times |
| Example 3 | 75 | 6 | 4.43 | 2.69 Times |
| Comparative Example 1 | 75 | 6 | 16.35 | — |

Experimental Example 1

Each of the reaction solutions according to the examples and the comparative example was sampled every 30 minutes, and the content of each of the organic matters was analyzed by gas chromatography. The content of the aldehyde dimer is shown in Table 2, and the amount of the aldehyde dimer before and after the reaction is shown in FIG. 4.

<Condition of GC Analysis>
1) Column: HP-1 (L: 30 m, ID: 0.32 mm, film: 1.05 m)
2) Injection volume: 1 μl
3) Inlet temp.: 250° C., pressure: 6.92 psi, total flow: 64.2 ml/min, split flow: 60 ml/min, spilt ratio: 50:1
4) Column flow: 1.2 ml/min
5) Oven temp.: 70° C./3 min-10° C./min-280° C./35 min
6) Detector temp.: 280° C., H2: 35 ml/min, air: 300 ml/min, He: 20 ml/min
7) GC model: Agilent 7890

TABLE 2

| | Aldehyde Dimer Content (% by Weight) | | |
|---|---|---|---|
| | Before Reaction | After Reaction | Increased Amount |
| Example 1 | 2.20 | 2.41 | 0.21 |
| Example 2 | 3.38 | 3.74 | 0.36 |
| Example 3 | 4.43 | 5.05 | 0.62 |
| Comparative Example 1 | 16.35 | 17.9 | 1.55 |

As shown by the results above, when the content of the aldehyde dimer is lower before the reaction, the content of the aldehyde dimer produced under the same condition decreases.

The method for preparing an aldehyde according to an exemplary embodiment of the present application comprises recirculating at least a portion of low-boiling point components separated from an upper part of a vaporizer catch pot back to the vaporizer catch pot. Accordingly, a concentration of high-boiling point components present in a section from the vaporizer catch pot to a hydroformylation reactor through a high-boiling point recirculation pipe may be lowered, a temperature of the solution may be lowered, and a time taken to reach the hydroformylation reactor may be reduced, and as a result, a content of an aldehyde dimer that may be synthesized in the section reaching the hydroformylation reactor through the high-boiling point recirculation pipe may be reduced.

According to an exemplary embodiment of the present application, the amount of produced aldehyde dimer may be reduced, and therefore, a reaction yield of the aldehyde preparation process may be enhanced.

The invention claimed is:

1. A method for preparing an aldehyde, the method comprising:
    reacting an olefin-based compound with a synthetic gas in a hydroformylation reactor in the presence of a catalyst to produce a reaction product comprising an aldehyde;
    introducing the reaction product to a vaporizer comprising a vaporizer catch pot;
    separating low-boiling point components of the reaction product from an upper part of the vaporizer catch pot;
    separating high-boiling point components of the reaction product from a lower part of the vaporizer catch pot; and
    recirculating at least a portion of the low-boiling point components separated from the upper part of the vaporizer catch pot back to the vaporizer catch pot,
    wherein a weight of the low-boiling point components recirculated to the vaporizer catch pot is from 0.1 times to 10 times a weight of the high-boiling point components separated from the lower part of the vaporizer catch pot.

2. A method for separating an aldehyde, the method comprising:
    introducing a composition comprising low-boiling point components comprising an aldehyde and high-boiling point components comprising a catalyst solution for a hydroformylation reaction to a vaporizer comprising a vaporizer catch pot;

separating the low-boiling point components comprising the aldehyde from an upper part of the vaporizer catch pot;

separating the high-boiling point components comprising the catalyst solution from a lower part of the vaporizer catch pot; and recirculating at least a portion of the low-boiling point components separated from the upper part of the vaporizer catch pot back to the vaporizer catch pot, wherein a weight of the low-boiling point components recirculated to the vaporizer catch pot is from 0.1 times to 10 times a weight of the high-boiling point components separated from the lower part of the vaporizer catch pot.

3. The method of claim 1, wherein the low-boiling point components separated from the upper part of the vaporizer catch pot comprises the aldehyde, an unreacted olefin-based compound and the synthetic gas.

4. The method of claim 1, wherein the high-boiling point components separated from the lower part of the vaporizer catch pot comprises an aldehyde dimer and the catalyst.

5. The method of claim 4, wherein the high-boiling point components separated from the lower part of the vaporizer catch pot is recirculated to the hydroformylation reactor.

6. The method of claim 4, wherein, an amount of the aldehyde dimer is 10% by weight or less based on a total weight of the high-boiling point components separated from the lower part of the vaporizer catch pot.

7. The method of claim 1, wherein the catalyst comprises a phosphite ligand represented by Chemical Formula 1 and a transition metal compound represented by Chemical Formula 2:

[Chemical Formula 1]

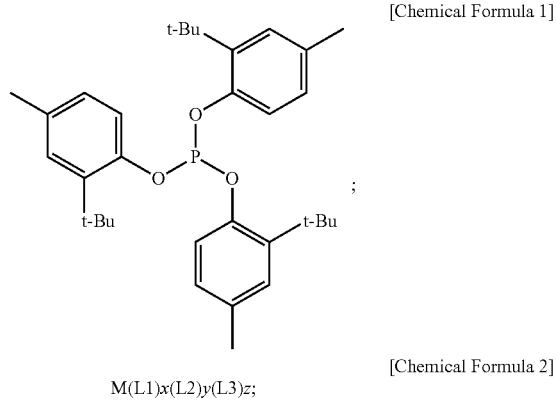

[Chemical Formula 2]

M(L1)$x$(L2)$y$(L3)$z$;

wherein in Chemical Formula 2,

M is selected from the group consisting of cobalt (Co), rhodium (Rh), iridium (Ir), ruthenium (Ru), iron (Fe), nickel (Ni), palladium (Pd), platinum (Pt) and osmium (Os);

L1, L2 and L3 are the same as or different from each other, and are independently selected from the group consisting of hydrogen, carbonyl (CO), cyclooctadiene, norbornene, chlorine, triphenylphosphine (TPP) and acetylacetonato (AcAc); and x, y and z are each independently 0 to 5, and x, y and z are not 0 at the same time.

8. The method of claim 1, wherein the olefin-based compound is represented by Chemical Formula 3:

[Chemical Formula 3]

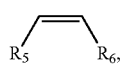

wherein in Chemical Formula 3, $R_5$ and $R_6$ are the same as or different from each other, and are independently selected from the group consisting of hydrogen, an alkyl group, fluorine (F), chlorine (Cl), bromine (Br), trifluoromethyl (—CF$_3$), and a substituted or unsubstituted aryl group.

9. The method of claim 1, wherein the olefin-based compound is one or more types selected from the group consisting of ethylene, propylene, 1-butene, 1-pentene, 1-hexene, 1-octene and styrene.

10. The method of claim 1, wherein the olefin-based compound is propylene, and the aldehyde is butyraldehyde.

11. An apparatus for preparing an aldehyde, the apparatus comprising:

a hydroformylation reactor comprising a reactant supply pipe and a reaction product moving pipe;

a vaporizer connected to the reaction product moving pipe and comprising a vaporizer catch pot;

a low-boiling point component pipe provided at an upper part of the vaporizer catch pot;

a high-boiling point component pipe provided at a lower part of the vaporizer catch pot; and a low-boiling point recirculation pipe connecting the low-boiling point component pipe and the vaporizer catch pot.

12. The apparatus of claim 11, further comprising a high-boiling point recirculation pipe connecting the high-boiling point component pipe and the hydroformylation reactor.

* * * * *